(12) United States Patent
Agbodoe

(10) Patent No.: US 6,638,280 B2
(45) Date of Patent: Oct. 28, 2003

(54) RONGEUR WITH DRAINAGE

(75) Inventor: Victor B. Agbodoe, Stougton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 09/974,405

(22) Filed: Oct. 10, 2001

(65) Prior Publication Data

US 2003/0069584 A1 Apr. 10, 2003

(51) Int. Cl.⁷ .............................................. A61B 17/00
(52) U.S. Cl. ........................ 606/83; 606/170; 606/167; 606/171
(58) Field of Search ............................ 606/83, 79, 167, 606/170, 171, 205, 206, 207, 184, 185, 107, 82, 190

(56) References Cited

U.S. PATENT DOCUMENTS

| | | |
|---|---|---|
| 2,113,246 A | 4/1938 | Wappler |
| 2,790,437 A | 4/1957 | Moore |
| 3,777,538 A | 12/1973 | Weatherly et al. |
| 3,814,102 A | 6/1974 | Thal |
| 4,043,343 A | 8/1977 | Williams |
| 4,084,594 A | 4/1978 | Mosior |
| 4,569,131 A | 2/1986 | Falk et al. |
| 4,722,338 A | 2/1988 | Wright et al. |
| 4,896,678 A | 1/1990 | Ogawa |
| 4,990,148 A | 2/1991 | Worrick, III et al. |
| 5,009,661 A | 4/1991 | Michelson |
| 5,026,375 A | 6/1991 | Linovitz et al. |
| 5,061,269 A | 10/1991 | Muller |
| 5,147,357 A | 9/1992 | Rose et al. |
| 5,147,378 A | 9/1992 | Markham |
| 5,156,608 A | 10/1992 | Troidl et al. |
| 5,273,519 A | 12/1993 | Koros et al. |
| 5,282,800 A | 2/1994 | Foshee et al. |
| 5,312,407 A | 5/1994 | Carter |
| 5,336,238 A | 8/1994 | Holmes et al. |
| 5,342,391 A | 8/1994 | Foshee et al. |
| 5,385,570 A | 1/1995 | Chin et al. |
| 5,451,227 A | 9/1995 | Michaelson |
| 5,484,441 A | 1/1996 | Koros et al. |
| 5,496,347 A | 3/1996 | Hashiguchi et al. |
| 5,507,772 A | 4/1996 | Shutt et al. |
| 5,507,774 A | 4/1996 | Holmes et al. |
| 5,527,339 A | 6/1996 | Koscher et al. |
| 5,569,258 A | 10/1996 | Gambale |
| 5,569,298 A | 10/1996 | Schnell |
| 5,582,618 A | 12/1996 | Chin et al. |
| 5,584,844 A | 12/1996 | Wesshaupt |
| 5,613,977 A | 3/1997 | Weber et al. |
| 5,618,308 A | 4/1997 | Holmes et al. |
| 5,630,832 A | 5/1997 | Giordano et al. |
| 5,649,958 A | 7/1997 | Grimm et al. |
| 5,653,713 A | 8/1997 | Michelson |
| 5,718,714 A | 2/1998 | Livneh |
| 5,766,177 A | 6/1998 | Lucas-Dean et al. |
| 5,851,214 A | 12/1998 | Larsen et al. |
| 5,879,365 A | 3/1999 | Whitfield et al. |
| 5,961,531 A | 10/1999 | Weber et al. |
| 6,063,103 A | 5/2000 | Hashiguchi |
| 6,077,290 A | 6/2000 | Marini |
| 6,126,674 A | 10/2000 | Janzen |
| 6,200,320 B1 | 3/2001 | Michelson |

FOREIGN PATENT DOCUMENTS

| | | |
|---|---|---|
| DE | 94 21125 U | 4/1995 |
| DE | 19748369 | 11/1999 |
| DE | 29922271 U1 | 12/1999 |

OTHER PUBLICATIONS

European Search Report EP02257006 dated Jan. 24, 2003.

*Primary Examiner*—Cary E. O'Connor
*Assistant Examiner*—Candice C. Melson

(57) ABSTRACT

A rongeur has one or more drainage holes through its shank into a space between its shank and crossbar to allow drainage of fluid therefrom and to enhance cleaning and sterilization.

10 Claims, 5 Drawing Sheets

RONGEUR WITH DRAINAGE

FIELD OF THE INVENTION

The present invention relates to a rongeur, and more particularly to a rongeur having drainage apertures.

BACKGROUND

The rongeur is a medical instrument used for a variety of purposes. It is particularly useful for removing small amounts of bone, cartilage or other body material from inside small spaces of the knee or between vertebrae. A rongeur usually includes a long fixed shank with an anvil or footplate at its distal end and a handle at its proximal end. A cross bar slideably engages the shank and reciprocates thereon by means of a pivotable second handle. Cutting edges on the distal end of the crossbar bite against the footplate to cut away a small portion of tissue with each reciprocation of the crossbar.

For precise operation of the instrument tight tolerances between the mating parts is preferred. While enhancing precise operation, these tolerances can make effective cleaning of the instrument difficult. Blood and other bodily matter with becomes trapped between the shank and crossbar can be difficult to remove. Failure to remove such matter can lead to incomplete sterilization. Accordingly, it is desirable to allow access to these parts during cleaning and sterilization.

The Janzen U.S. Pat. No. 6,126,674, incorporated herein by reference, attempts to solve this problem by providing a removable crossbar. A slot in the top of the pivotable handle receives a pin on the crossbar. A rotating disc on the fixed handle abuts a surface on the pivotable handle to limit spread between the handles. Rotation of the disc into an alternate orientation allow a slightly broader spread between the handles allowing the crossbar to move back distally off of the pin and to then be removed. Nevertheless, in some instances, operating personnel may forget to disassemble the rongeur.

SUMMARY OF THE INVENTION

A rongeur according to the present invention overcomes these and other limitations of the prior art. It comprises an elongated shank having a distal end and a proximal end and a footplate at the distal end of the elongated shank. An elongated crossbar is adapted to reciprocate axially with respect to the shank. It has a distal end and a proximal end and a cutting surface at its distal end whereby to cut tissue between the cutting surface and the footplate. One or more drainage apertures penetrate through the shank into a space between the shank and the crossbar.

Preferably a plurality of apertures penetrate the shank into the space between the shank and the crossbar. They may be located adjacent the footplate. In one preferred aspect of the invention, the shank has a slot on an upper surface thereof and the crossbar has a spline on a lower surface thereof, with the spline being disposed within the slot, and drainage apertures penetrating the shank into the slot.

Preferably, the drainage holes are countersunk facing the crossbar whereby to encourage drainage of liquid into the one or more holes. The surface facing the crossbar through which the holes penetrate may be sloped toward the drainage holes to encourage liquid to drain therethrough.

A method, according to the present invention, is provided for sterilizing a rongeur comprising an elongated shank having a distal end and a proximal end, a footplate at the distal end of the elongated shank, and an elongated crossbar adapted to reciprocate axially with respect to the shank, the crossbar having a distal end and a proximal end and a cutting surface at its distal end whereby to cut tissue between the cutting surface and the footplate. The method comprises the steps of subjecting the rongeur to a sterilizing fluid and passing the sterilizing fluid into a space between the crossbar and shank through one or more apertures through the shank. The sterilizing fluid can be steam. The sterilizing fluid can be drained from the space through the apertures, as for instance steam condensate.

DETAILED DESCRIPTION

Figure 1:
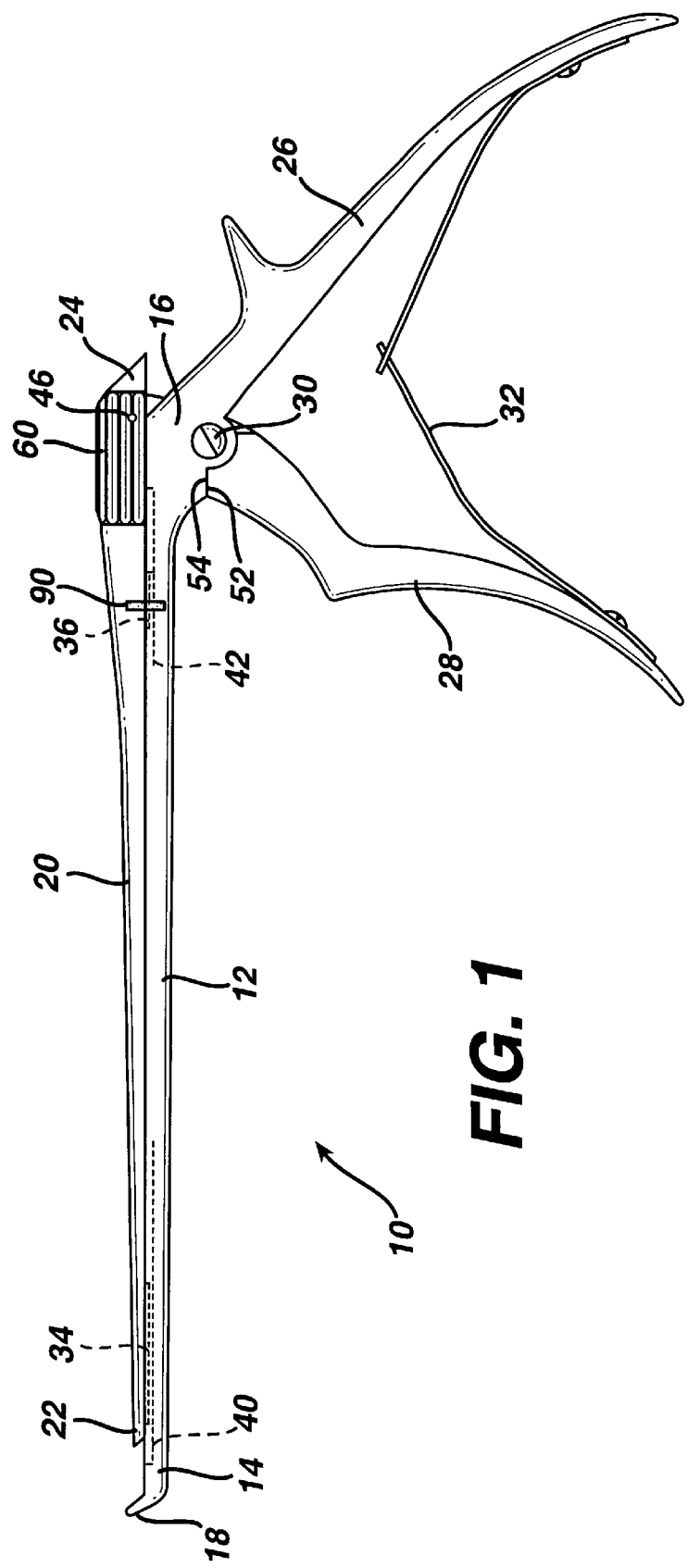
FIG. 1 is a front elevation view of a rongeur according to the present invention.

FIG. 1 illustrates a rongeur 10 according to the present invention. It comprises an elongated shank 12 having a distal end 14 and proximal end 16. A footplate 18 extends upwardly from the shank 12 at its distal end 14. A crossbar 20 slideably engages the shank 12 and also comprises a distal end 22 and proximal end 24. A first handle 26 extends downwardly from the shank proximal end 16 in fixed relation to the shank 12. A second handle 28 pivotably attaches to the shank 12 near its proximal end 16 and pivots about an axis 30. A spring 32 between the first and second handles 26 and 28 biases them apart.

Figure 2:
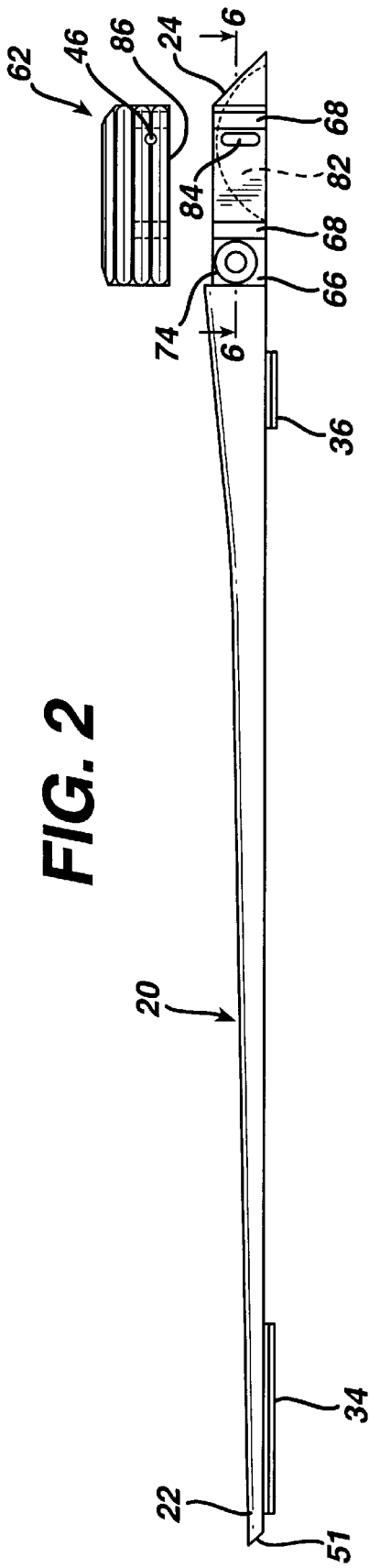
FIG. 2 is a front elevation view of a crossbar from the rongeur of FIG. 1.
Figure 3:
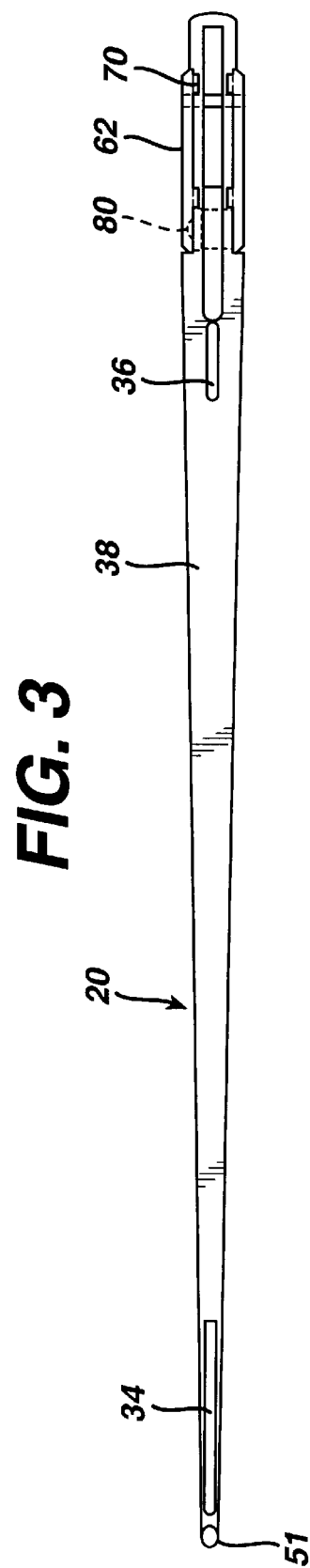
FIG. 3 is a bottom plan view of the crossbar of FIG. 2.

As further seen in FIGS. 2 and 3, distal and proximal T-shaped splines 34 and 36, respectively, on a lower surface 38 of the crossbar 20 fit within respective distal and proximal T-shaped slots, 40 and 42, respectively, on an upper surface 44 of the shank 12 to allow slideable axial movement between the crossbar 20 and shank 12 without allowing the crossbar 20 to lift off of the shank 12. It will be appreciated by one of skill in the art that the locations of the splines and slots can be reversed and that other engaging shapes can be substituted therefor.

Figure 4:
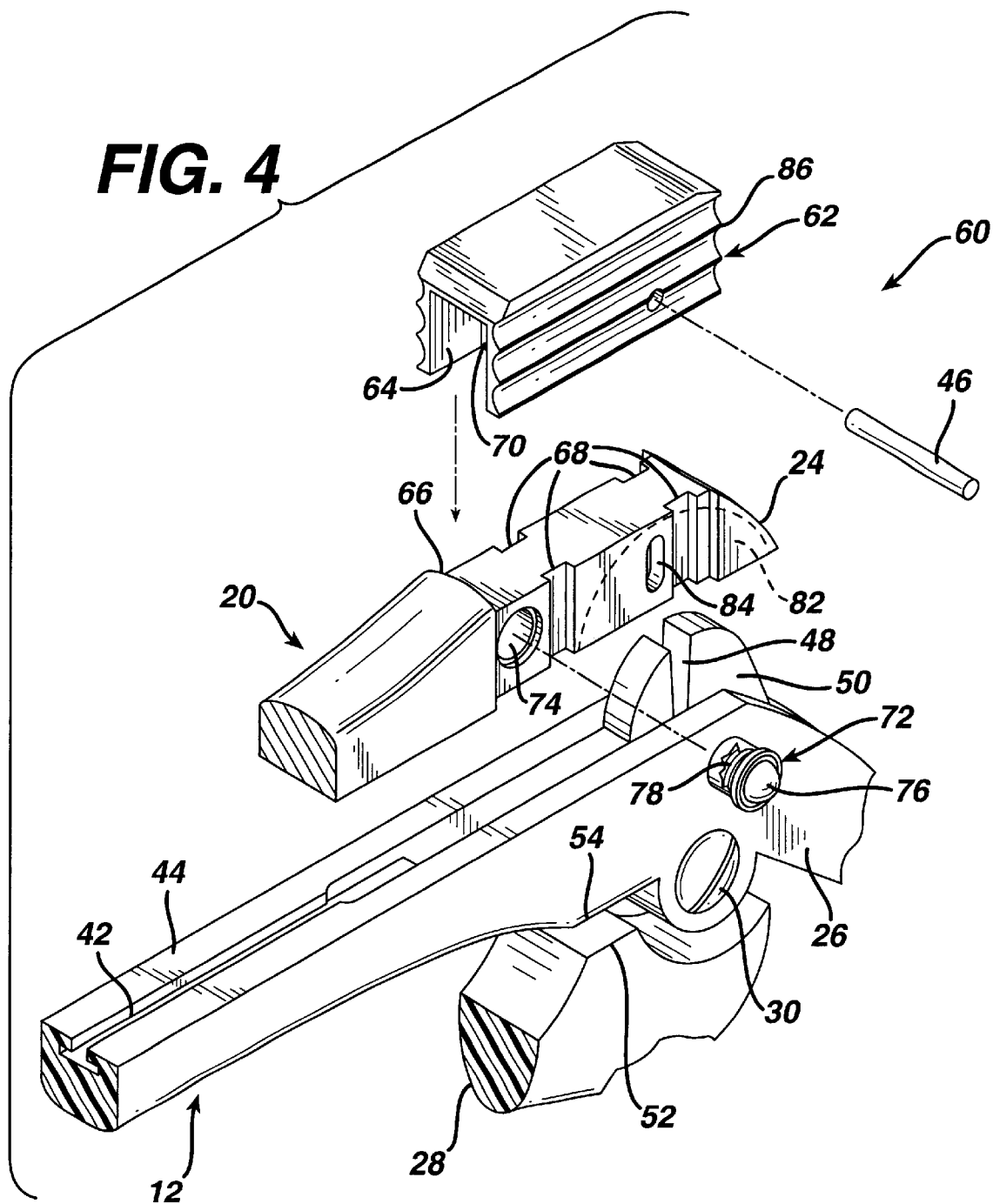
FIG. 4 is an exploded perspective view of a locking mechanism of the rongeur of FIG. 1.
Figure 5:
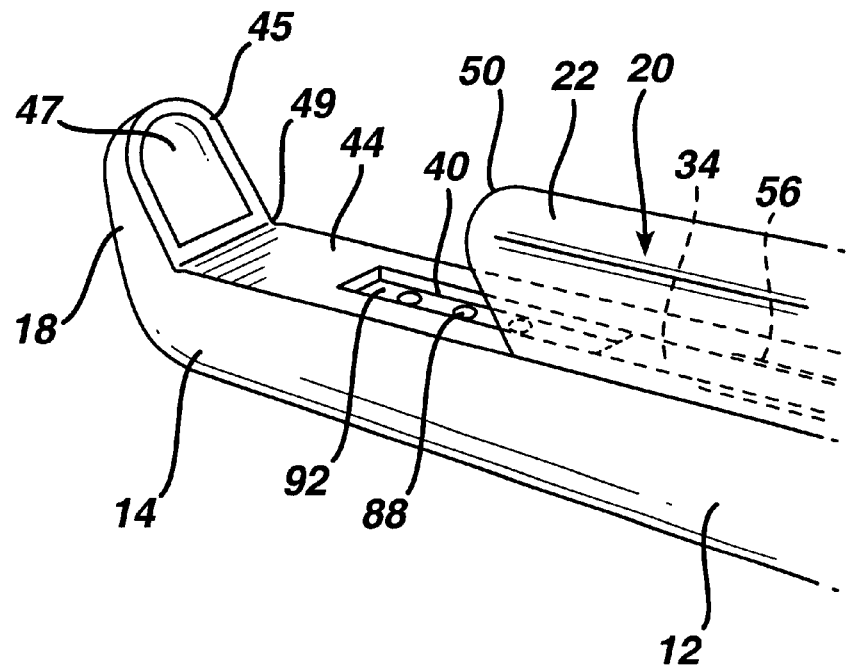
FIG. 5 is a perspective detail view of a footplate on the rongeur of FIG. 1

Turning further to FIG. 4, a pin 46 on the crossbar 20 rides within a slot 48 on an upper portion 50 of the second handle 28 so that when the second handle 28 is squeezed toward the first handle 26 by an operator the slot 48 moves distally and the action of the pin 46 therein drives the crossbar 20 distally. Turning further to FIG. 5, the footplate 18 comprises an anvil cutting surface 45 about a tissue receiving recess 47 and a stress relieving groove 49 between the footplate 18 and shank 12 as more fully described in U.S. Pat. No. 4,990,148 to Worrick, III et al., fully incorporated herein by reference. Cutting edges 51 on the distal end 22 of the crossbar 20 engage the anvil surface 45 whereby tissue, as for instance bone, trapped therebetween is cut.

It is advantageous to disassemble the rongeur 10, by removing the crossbar 20, prior to cleaning and sterilizing. Focusing primarily upon FIG. 4, removal of the crossbar 20 is effected by moving the pin 46 upwardly out of the slot 48. Contact between a handle abutment surface 52 on the second handle 28 and a shank abutment surface 54 on the shank 12 limits rotation of the second handle 28 and thus effectively limits rearward or proximal movement of the crossbar 20. Proximal portions 56 and 58 respectively of the distal slot 40 and proximal slot 42 are open, not T-shaped, so as to allow disengagement of the splines 34 and 36 from the slots 40 and 42 and thereby allow the crossbar 20 to be lifted off of the shank 12. To disengage the splines 34 and 36 they must be in register with the proximal portions 56 and 58. However, abutment of the handle and shank abutment surfaces 52 and 54 limits proximal movement of the crossbar 20 sufficiently to disallow registry of the splines 34 and 36 with the proximal portions 56 and 58. Moving the pin 46 upwardly out of the slot 48 allows further proximal movement of the crossbar 20 so as to allow registry of the splines 34 and 36 with the proximal portions 56 and 58 and thus removal of the crossbar 20.

Figure 6:
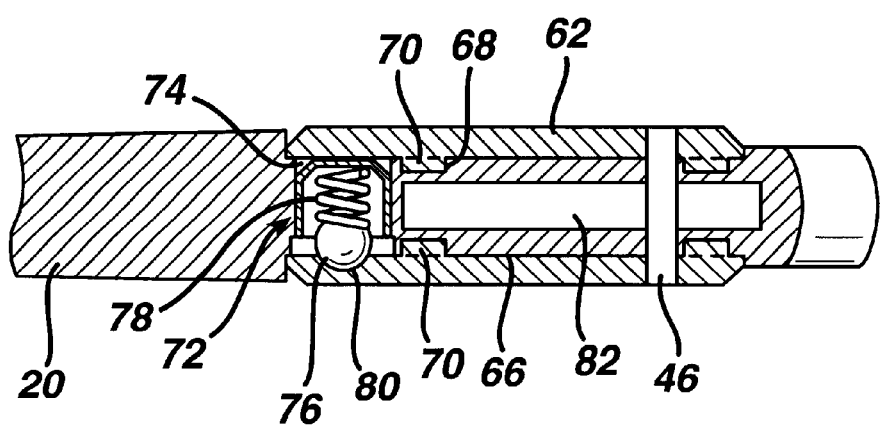
FIG. 6 is a cross sectional view taken along lines 6—6 of FIG. 2.

A locking mechanism 60 maintains the pin 46 within the slot 48 and allows its selective movement thereout. The locking mechanism 60 comprises a channel member 62 having a lower channel 64 which fits over a recessed portion 66 of the crossbar 20 near its proximal end 24. Vertically oriented guiding grooves 68 on the recessed portion 66 receive mating tongues 70 to guide vertical movement of the channel member 62 on the crossbar 20. The pin 46 passes laterally through the channel member 62 and is affixed thereto. A spring ball plunger 72 on the received within an aperture 74 on the crossbar comprises a caged ball 76 and spring 78 (see also FIG. 6). The ball 76 engages a dimple 80 on an inner surface 82 of the channel 64 to hold the channel member in a lowered position. Sufficient upward force on the channel member 62 disengages the ball 76 from the dimple 80 to allow the channel member 62 to move upwardly.

Figure 7:
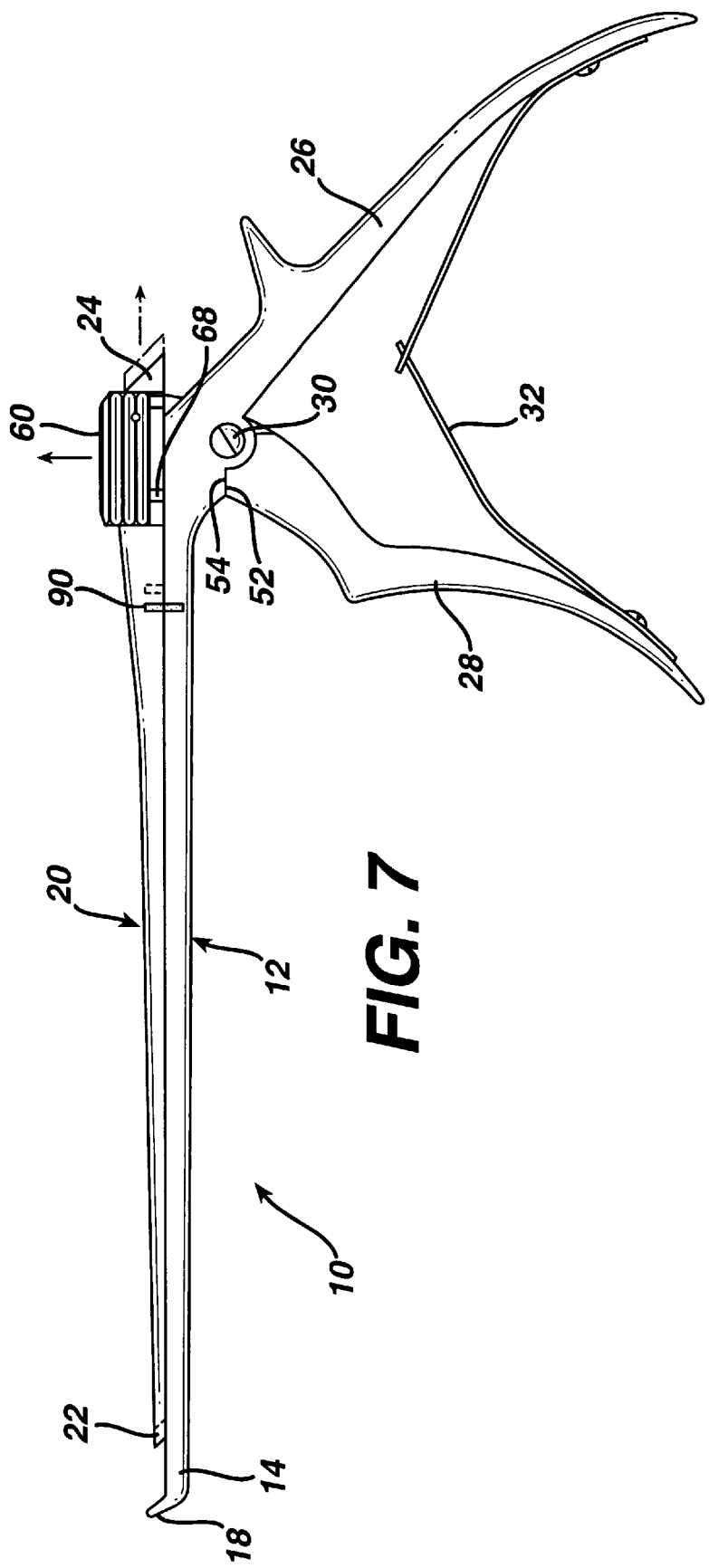
FIG. 7 is a front elevation view of the rongeur of FIG. 1 showing the locking mechanism in the unlocked orientation.

As primarily seen in FIGS. 2 and 4, an arcuate undercut chamber 82 on the crossbar 20 receives the second handle upper portion 50. The pin 46 passes through elongated vertical slots 84 in the crossbar 20 and sits in the slot 48 in the second handle upper portion 50. With the pin 46 trapped in the elongated slots 84 the channel member 62 is thus held to the crossbar 20, even when lifted to an upper position as shown in FIG. 7. Preferably, gripping enhancements such as ribbing 86 shown in FIG. 4 is provided on the channel member 62.

Figure 8:
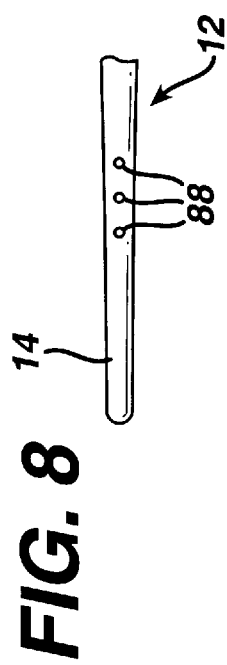
FIG. 8 is a bottom plan view of a distal portion of the rongeur of FIG. 1

Turning primarily to FIG. 8, drainage holes 88 penetrate the shank 12 near its distal end 14. These drainage holes allow drainage of blood and bodily fluids during use and allow drainage during cleaning. They may be countersunk on a surface 92 facing the crossbar 20 as shown in FIG. 5 to encourage drainage into the holes 88. Further, the surface 92 can be sloped toward the holes 88 to enhance drainage therethrough.

In use, the first and second handles 26 and 28 are squeezed together to move the second handle upper portion 50 distally thereby engaging the pin 46 and driving the crossbar 20 distally. The cutting edges 51 on the crossbar distal end 22 move toward the anvil 45 and tissue (not shown) trapped therebetween is cut away. Typically, many successive cuts are made in one procedure. Blood and bodily fluid within the distal slot 40 are allowed to pass out through the drainage holes 88. After the cutting procedure is over, the channel member 62 is lifted up and the crossbar moved proximally to a retracted release position, as shown in phantom in FIG. 7. In this position the T-shaped splines 34 and 36 align with the open proximal portions 56 and 58 of the slots 40 and 42. The crossbar 20 is then lifted free of the shank 12. Cleaning and sterilization of the rongeur 10 is effected in this disassembled state. Preferably, the sterilization is performed with the rongeur sealed within a bacteria proof enclosure having provision to pass a steriliant therethrough, such as a tray wrapped with Central Supply Room (CSR) wrap, or a TYVEK® (spun bonded olefin)/MYLAR (polyester film) pouch.

If the rongeur 10 is not disassembled prior to cleaning and sterilization, the drainage holes 88 will allow cleaning solutions to enter the difficult to clean space between the shank 10 and crossbar 20 and will allow sterilizing fluids, such as steam or chemical steriliants such as vapor phase hydrogen peroxide or ethylene oxide, to enter the space to effect sterilization of the surfaces therein.

To reassemble the rongeur 10, the channel member 62 is placed in its upward position and the splines 34 and 36 are moved into the proximal portions 56 and 58 of the slots 40 and 42. The crossbar is moved distally to engage the T-shaped splines 34 and 36 within the T-shaped slots 40 and 42 and to place the pin 46 in location over the slot 48 on the second handle upper portion 50. A pair of alignment marks 90 on the shank 12 and crossbar 20 can be provided to assist in locating this position. Then, the channel member is pressed down to engage the pin 46 into the slot 48 and the spring ball plunger 72 into the dimple 80.

The invention now being fully described, it will be apparent to one of ordinary skill in the art that many modifications and changes can be made thereto without departing from the spirit or scope of the invention as defined in the following claims.

What is claimed is:

1. A rongeur comprising:
    an elongated shank having a distal end and a proximal end;
    a footplate at the distal end of the elongated shank;
    an elongated crossbar adapted to reciprocate axially with respect to the shank, the crossbar having a distal end and a proximal end and a cutting surface at its distal end whereby to cut tissue between the cutting surface and the footplate; and
    one or more drainage apertures through the shank into a space between the shank and the crossbar.

2. A rongeur according to claim 1 wherein a plurality of apertures penetrate the shank into the space between the shank and the crossbar.

3. A rongeur according to claim 1 wherein the one or more drainage apertures are countersunk facing the crossbar whereby to encourage drainage of liquid into the one or more drainage apertures.

4. A rongeur according to claim 1 wherein a surface facing the crossbar through which penetrate the one or more drainage apertures slopes toward the one or more drainage apertures to encourage liquid to drain into the one or more drainage apertures.

5. A rongeur according to claim 1 wherein the one or more apertures are adjacent the footplate.

6. A rongeur according to claim 5 wherein the shank comprises a slot on an upper surface thereof and the crossbar comprises a spline on a lower surface thereof, the spline being disposed within the slot, and wherein the one or more drainage apertures penetrate the shank into the slot.

7. A method of sterilizing a rongeur comprising an elongated shank having a distal end and a proximal end, a footplate at the distal end of the elongated shank, and an elongated crossbar adapted to reciprocate axially with respect to the shank, the crossbar having a distal end and a proximal end and a cutting surface at its distal end whereby to cut tissue between the cutting surface and the footplate, the method comprising the steps of:

subjecting the rongeur to a sterilizing fluid; and passing the sterilizing fluid into a space between the crossbar and shank through one or more apertures through the shank.

8. A method according to claim 7 wherein the sterilizing fluid is steam.

9. A method according to claim 7 and further comprising the step of draining sterilizing fluid from the space through the apertures.

10. A method according to claim 7 wherein the apertures are adjacent the footplate.

* * * * *